United States Patent
Fielder et al.

(10) Patent No.: US 10,507,316 B2
(45) Date of Patent: Dec. 17, 2019

(54) IMPLANTABLE FLUID ROUTER

(75) Inventors: Paul D. Fielder, Chalford Hill (GB); David E. Johnson, Milbury Heath (GB); Maxwell R. Woolley, Bristol (GB)

(73) Assignee: RENISHAW (IRELAND) LIMITED, Wotton-under-Edge (GB)

( * ) Notice: Subject to any disclaimer, the term of this patent is extended or adjusted under 35 U.S.C. 154(b) by 636 days.

(21) Appl. No.: 13/575,759

(22) PCT Filed: Feb. 11, 2011

(86) PCT No.: PCT/GB2011/000182
§ 371 (c)(1),
(2), (4) Date: Jul. 27, 2012

(87) PCT Pub. No.: WO2011/098768
PCT Pub. Date: Aug. 18, 2011

(65) Prior Publication Data
US 2012/0310182 A1    Dec. 6, 2012

(30) Foreign Application Priority Data
Feb. 12, 2010    (GB) .................................. 1002370.3

(51) Int. Cl.
*A61M 25/14*    (2006.01)
*A61M 39/02*    (2006.01)
(Continued)

(52) U.S. Cl.
CPC ..... *A61M 39/0247* (2013.01); *A61B 17/1739* (2013.01); *A61M 5/14276* (2013.01);
(Continued)

(58) Field of Classification Search
CPC .......... A61M 39/0247; A61M 5/14276; A61M 5/36; A61M 2039/0276;
(Continued)

(56) References Cited

U.S. PATENT DOCUMENTS 4,013,074 A    3/1977  Siposs
4,511,355 A *  4/1985  Franetzki et al. ............ 604/131
(Continued)

FOREIGN PATENT DOCUMENTS

CN    2684843 Y    3/2005
CN    2834581 Y    11/2006
(Continued)

OTHER PUBLICATIONS

Nov. 14, 2014 Office Action issued in Japanese Application No. 2012-552462.
(Continued)

*Primary Examiner* — Quynh-Nhu H. Vu
(74) *Attorney, Agent, or Firm* — Oliff PLC

(57) ABSTRACT

An implantable fluid router is described that includes one or more inlets, one or more outlets and at least one gas vent for removing gas from liquid routed from the one or more inlets to the one or more outlets, The implantable router may be used with implantable drug delivery apparatus. A catheter device including such a fluid router is also described.

17 Claims, 5 Drawing Sheets

Figure 1:
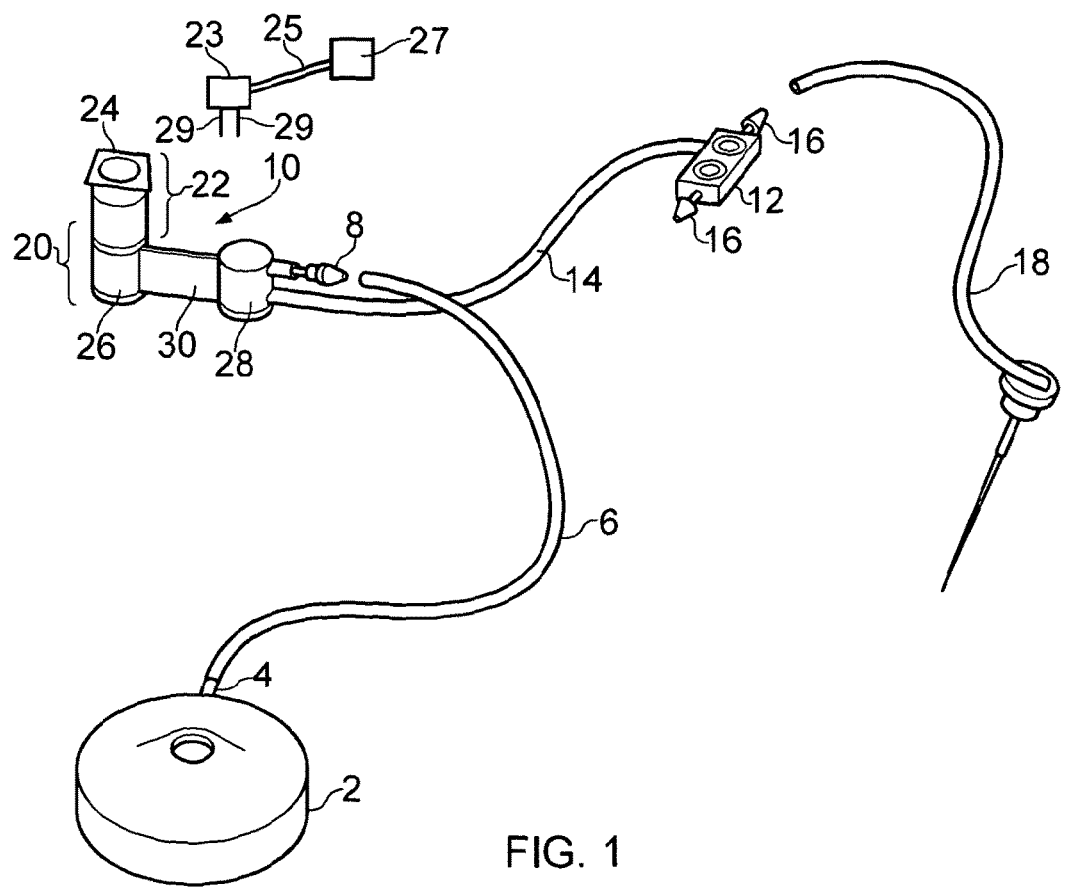

(51) Int. Cl.
  *A61M 5/142* (2006.01)
  *A61M 5/36* (2006.01)
  *A61B 17/17* (2006.01)
  *A61M 39/10* (2006.01)
  *A61M 39/22* (2006.01)

(52) U.S. Cl.
  CPC ............. *A61M 5/36* (2013.01); *A61M 39/105* (2013.01); *A61M 39/223* (2013.01); *A61M 2039/0261* (2013.01); *A61M 2039/0276* (2013.01); *A61M 2039/0282* (2013.01); *A61M 2039/1083* (2013.01); *A61M 2039/1088* (2013.01); *A61M 2205/02* (2013.01); *A61M 2205/7518* (2013.01); *A61M 2210/0687* (2013.01)

(58) Field of Classification Search
  CPC ...... A61M 2205/7518; A61M 2205/02; A61M 2039/0261; A61M 2210/0687; A61M 39/223; A61M 2039/1088; A61M 39/105; A61M 2039/0282; A61B 17/1739
  USPC ................. 604/891.1, 288.01, 264, 93.01
  See application file for complete search history.

(56) References Cited

U.S. PATENT DOCUMENTS

| | | | |
|---|---|---|---|
| 4,578,063 A | 3/1986 | Inman et al. | |
| 4,634,422 A | 1/1987 | Kantrowitz et al. | |
| 4,692,147 A | 9/1987 | Duggan | |
| 4,695,273 A | 9/1987 | Brown | |
| 4,705,464 A | 11/1987 | Arimond | |
| 4,772,263 A * | 9/1988 | Dorman | A61M 5/14276 |
| | | | 128/DIG. 12 |
| 4,790,826 A | 12/1988 | Elftman | |
| 4,822,339 A * | 4/1989 | Tran | A61M 5/1407 |
| | | | 604/246 |
| 4,897,081 A | 1/1990 | Poirier et al. | |
| 4,903,707 A | 2/1990 | Knute et al. | |
| 5,098,397 A | 3/1992 | Svensson et al. | |
| 5,120,313 A | 6/1992 | Elftman | |
| 5,122,114 A | 6/1992 | Miller et al. | |
| 5,171,216 A | 12/1992 | Dasse et al. | |
| 5,221,474 A | 6/1993 | Yokono et al. | |
| 5,318,545 A | 6/1994 | Tucker | |
| 5,352,207 A | 10/1994 | Nussbaum | |
| 5,549,581 A * | 8/1996 | Lurie | A61M 25/0041 |
| | | | 600/374 |
| 5,695,490 A * | 12/1997 | Flaherty | A61M 39/0208 |
| | | | 128/DIG. 12 |
| 5,752,930 A | 5/1998 | Rise et al. | |
| 5,782,645 A | 7/1998 | Stobie et al. | |
| 5,833,655 A | 11/1998 | Freed et al. | |
| 5,836,935 A | 11/1998 | Ashton et al. | |
| 5,906,596 A | 5/1999 | Tallarida | |
| 5,916,200 A | 6/1999 | Eppley et al. | |
| 5,954,687 A * | 9/1999 | Baudino | A61M 25/02 |
| | | | 604/174 |
| 5,990,382 A | 11/1999 | Fox | |
| 6,013,051 A * | 1/2000 | Nelson | A61M 39/0208 |
| | | | 604/247 |
| 6,018,094 A | 1/2000 | Fox | |
| 6,044,304 A * | 3/2000 | Baudino | A61N 1/0539 |
| | | | 600/378 |
| 6,086,555 A * | 7/2000 | Eliasen | A61M 39/0208 |
| | | | 604/175 |
| 6,134,477 A | 10/2000 | Knuteson | |
| 6,152,933 A | 11/2000 | Werp et al. | |
| 6,347,711 B1 * | 2/2002 | Goebel | A61M 5/38 |
| | | | 210/436 |
| 6,356,792 B1 | 3/2002 | Errico et al. | |
| 6,454,774 B1 | 9/2002 | Fleckenstein | |
| 6,471,689 B1 | 10/2002 | Joseph et al. | |
| 6,607,504 B2 | 8/2003 | Haarala et al. | |
| 6,609,020 B2 | 8/2003 | Gill | |
| 6,685,674 B2 | 2/2004 | Douglas et al. | |
| 6,758,841 B2 | 7/2004 | Haarala et al. | |
| 6,840,919 B1 | 1/2005 | kansson | |
| 6,852,106 B2 | 2/2005 | Watson et al. | |
| 7,331,940 B2 | 2/2008 | Sommerich | |
| 7,351,239 B2 * | 4/2008 | Gill | A61M 5/14232 |
| | | | 604/288.01 |
| 7,604,658 B2 | 10/2009 | Wilson et al. | |
| 7,833,204 B2 | 11/2010 | Picha | |
| 8,323,270 B2 | 12/2012 | Shachar et al. | |
| 8,827,987 B2 | 9/2014 | Fielder et al. | |
| 8,974,422 B2 | 3/2015 | Gill et al. | |
| 9,439,774 B2 | 9/2016 | de Villiers et al. | |
| 2002/0133232 A1 | 9/2002 | Ricci et al. | |
| 2003/0004520 A1 | 1/2003 | Haarala et al. | |
| 2003/0023208 A1 | 1/2003 | Osypka et al. | |
| 2003/0120215 A1 | 6/2003 | Bousquet | |
| 2003/0130577 A1 | 7/2003 | Purdy et al. | |
| 2003/0171711 A1 | 9/2003 | Rohr et al. | |
| 2003/0171738 A1 | 9/2003 | Konieczynski et al. | |
| 2004/0034367 A1 | 2/2004 | Malinowski | |
| 2004/0243064 A1 | 12/2004 | Sommerich | |
| 2004/0249361 A1 | 12/2004 | Denoth et al. | |
| 2004/0260361 A1 | 12/2004 | Gibson | |
| 2004/0267238 A1 | 12/2004 | Haarala et al. | |
| 2005/0075624 A1 | 4/2005 | Miesel | |
| 2005/0143800 A1 | 6/2005 | Lando et al. | |
| 2005/0182420 A1 | 8/2005 | Schulte et al. | |
| 2005/0203486 A1 | 9/2005 | Sommerich | |
| 2005/0245887 A1 | 11/2005 | Olsen et al. | |
| 2005/0267591 A1 | 12/2005 | Ricci et al. | |
| 2005/0283203 A1 | 12/2005 | Flaherty et al. | |
| 2006/0122578 A1 | 6/2006 | Lord et al. | |
| 2007/0255262 A1 * | 11/2007 | Haase | 604/891.1 |
| 2008/0287910 A1 | 11/2008 | Picha | |
| 2009/0030373 A1 | 1/2009 | Gill | |
| 2009/0082758 A1 * | 3/2009 | Gill | A61M 5/14276 |
| | | | 604/891.1 |
| 2009/0187149 A1 | 7/2009 | Nelson | |
| 2009/0205641 A1 * | 8/2009 | Tanaka | A61M 1/04 |
| | | | 128/200.24 |
| 2009/0227989 A1 | 9/2009 | Burke et al. | |
| 2010/0042070 A1 | 2/2010 | Gill et al. | |
| 2010/0069892 A1 | 3/2010 | Steinbach et al. | |
| 2010/0145162 A1 | 6/2010 | Devauchelle et al. | |
| 2010/0217236 A1 | 8/2010 | Gill et al. | |
| 2012/0310182 A1 | 12/2012 | Fielder et al. | |
| 2014/0343500 A1 | 11/2014 | Fielder et al. | |
| 2014/0371679 A1 | 12/2014 | Woolley et al. | |

FOREIGN PATENT DOCUMENTS

| | | |
|---|---|---|
| CN | 201088751 Y | 7/2008 |
| CN | 101384286 A | 3/2009 |
| CN | 101400386 A | 4/2009 |
| CN | 101537224 A | 9/2009 |
| CN | 101541356 A | 9/2009 |
| DE | 20115120 U1 | 3/2002 |
| DE | 10143820 A1 | 3/2003 |
| EP | 0266243 A1 | 5/1988 |
| EP | 0 992 257 A1 | 4/2000 |
| EP | 1426074 A1 | 6/2004 |
| EP | 1 481 697 A1 | 12/2004 |
| EP | 1576975 A1 | 9/2005 |
| EP | 1704891 A2 | 9/2006 |
| FR | 2690625 A1 | 11/1993 |
| FR | 2750054 A1 | 12/1997 |
| GB | 2389791 A | 12/2003 |
| GB | 2459101 A | 10/2009 |
| JP | S48-5290 A | 1/1973 |
| JP | S62-240069 A | 10/1987 |
| JP | H02-168968 A | 6/1990 |
| JP | H03-126438 A | 5/1991 |
| JP | H03-286776 A | 12/1991 |
| JP | H05-42220 A | 2/1993 |
| JP | H08-141088 A | 6/1996 |
| JP | H11-504231 A | 4/1999 |

(56) References Cited

FOREIGN PATENT DOCUMENTS

| JP | 2001-505115 A | 4/2001 |
|---|---|---|
| JP | 2001-509063 A | 7/2001 |
| JP | 2004-000495 A | 1/2004 |
| JP | 2006-520656 A | 9/2006 |
| JP | 2006-263470 A | 10/2006 |
| JP | 2006-525827 A | 11/2006 |
| JP | 2009-526589 A | 7/2009 |
| JP | 2009-219889 A | 10/2009 |
| WO | WO 89/07467 A1 | 8/1989 |
| WO | 96/29953 A1 | 10/1996 |
| WO | WO 97/49438 A1 | 12/1997 |
| WO | 98/31417 A2 | 7/1998 |
| WO | WO 99/34754 A1 | 7/1999 |
| WO | WO 01/12158 A1 | 2/2001 |
| WO | WO 03/077784 A1 | 9/2003 |
| WO | WO 03/077785 A1 | 9/2003 |
| WO | 2004/084768 A2 | 10/2004 |
| WO | WO 2004/105839 A1 | 12/2004 |
| WO | WO 2007/093778 A1 | 8/2007 |
| WO | WO 2007/104953 A1 | 9/2007 |
| WO | WO 2007/104961 A1 | 9/2007 |
| WO | WO 2008/062173 A1 | 5/2008 |
| WO | WO 2009/047494 A1 | 4/2009 |
| WO | WO 2009/094389 A1 | 7/2009 |
| WO | 2009/103758 A2 | 8/2009 |
| WO | WO 2009/096851 A1 | 8/2009 |
| WO | WO 2009/128959 A1 | 10/2009 |
| WO | WO 2011/098769 A1 | 8/2011 |

OTHER PUBLICATIONS

Feb. 25, 2015 Office Action issued in Chinese Application No. 201180009002.1.
Oct. 18, 2013 Office Action issued in U.S. Appl. No. 13/575,769.
Feb. 24, 2014 Office Action issued in U.S. Appl. No. 13/575,769.
Mar. 3, 2014 Office Action issued in Chinese Application No. 201180009336.9 (with partial translation).
Lundgren et al. "Soft-Tissue-Anchored Percutaneous Device for Long-Term Intracorporeal Access." Journal of Investigative Surgery. vol. 2, pp. 17-27.1989.
Fricova et al. "The Implantable Intravenous Ports". Bolest. 2006. pp. 165-172.
Nyman et al. "Soft-Tissue-Anchored Transcutaneous Port for Long-Term Percutaneous Transhepatic Biliary Drainage". CardioVascular and Interventional Radiology. vol. 28, pp. 53-59. 2005.
Berntorp et al. "Experience with a new percutaneous port system, Percuseal, for intravenous injection in patients with haemophilia, von Willebrand disease and severe alpha.sub.1-antitrypsin deficiency". Haemophilia. vol. 9, pp. 173-178. 2003.
Germano et al. "Surgical Techniques for Stereotactic Implant of Deep Brain Stimulators". Seminars in Neurosurgery. vol. 12, No. 2, pp. 213-223. 2001.
"Lead Kit for Deep Brain Stimulation". Medtronic Manual, pp. 9-56. 2002.
May 6, 2013 Chinese Office Action issued in Application No. 201210084254.7.
Jul. 6, 2012 Office Action issued in Japanese Patent Application No. 2009-537691.
Mar. 25, 2014 Office Action issued in Chinese Application No. 201210084254.7.
Sep. 20, 2013 Office Action issued in Japanese Application No. 2009-537691.
Dec. 12, 2014 Office Action issued in Canadian Application No. 2,670,164.
Nov. 15, 2014 Office Action issued in Chinese Application No. 201210084254.7.
U.S. Appl. No. 14/581,549, filed Dec. 23, 2014 in the name of Gill et al.
U.S. Appl. No. 14/431,133, filed Mar. 25, 2015 in the name of Woolley et al.

May 9, 2014 Office Action issued in U.S. Appl. No. 12/312,584.
Dec. 18, 2013 Office Action issued in U.S. Appl. No. 12/312,584.
Aug. 10, 2011 Office Action issued in U.S. Appl. No. 12/312,584.
Dec. 6, 2010 Office Action issued in U.S. Appl. No. 12/312,584.
Apr. 4, 2008 International Search Report issued in International Patent Application No. PCT/GB2007/004438.
Jun. 30, 2011 Written Opinion of International Search Report issued in International Patent Application No. PCT/GB2011/000183.
Jun. 30, 2011 Written Opinion of International Search Report issued in International Patent Application No. PCT/GB2011/000182.
Jan. 31, 2014 International Search Report issued in International Patent Application No. PCT/GB2013/052559.
Dec. 31, 2012 Search Report issued in GB Patent Application No. 1217606.01.
Jan. 31, 2014 Written Opinion of International Search Report issued in International Patent Application No. PCT/GB2013/052559.
U.S. Appl. No. 14/445,626, filed Jul. 29, 2014 in the name of Fielder et al.
Apr. 4, 2008 Written Opinion of International Search Report Issued in PCT/GB2007/004438.
Chinese Office Action issued in Chinese Application No. 201180009002.1 dated Jun. 23, 2014 (with translation).
Chinese Office Action issued in Chinese Patent Application No. 201180009002.1 dated Aug. 16, 2013 (with translation).
Chinese Office Action issued in Chinese Patent Application No. 201180009336.9 on Jul. 25, 2013 (with translation).
Jun. 30, 2011 Search Report issued in PCT/GB2011/000183.
Jun. 30, 2011 Search Report issued in PCT/GB2011/000182.
Fielder et al; U.S. Appl. No. 13/575,769, filed Jul. 27, 2012.
May 21, 2010 Search Report issued in Patent Application No. GB1002370.3.
N.K.O. & Hoofd-Halsheelkunde, "Bone Anchored Hearing Aids (B.A.H.A.)," http://www.nko.uza.be/prof/baha/index.html, Oct. 11, 2008, 5 pages.
Borenstein, Jeffrey T., "Medicine by Micromachine," IEEE Spectrum, Nov. 2009, Int, pp. 35-39.
Bovo, R., "Simplified technique without skin flap for the bone-anchored hearing aid (BAHA) implant," Technical Note, ACTA Otorhinolaryngologica Italica 2008;28, pp. 252-255, Ferrara, Italy.
Oct. 9, 2014 Office Action issued in Japanese Application No. 2012-552463.
Dec. 11, 2015 Search Report issued in European Application No. 15 18 1867.
Jul. 1, 2015 Office Action issued in Chinese Application No. 201210084254.7.
May 17, 2016 Office Action issued in European Application No. 11 706 900.5.
May 13, 2016 Office Action issued in Chinese Application No. 201210084254.7.
Jul. 20, 2016 Office Action issued in Chinese Patent Application No. 201380051627.3.
Nov. 4, 2016 Office Action Issued in U.S. Appl. No. 14/445,626.
Nov. 4, 2016 Office Action issued in Chinese Patent Application No. 201410772721.4
Apr. 26, 2016 Office Action Issued in U.S Appl. No. 14/445,626.
May 2, 2016 Office Action issued in Japanese Application No. 2015-166782.
Jun. 22, 2016 Office Action issued in U.S. Appl. No. 14/431,133.
May 17, 2017 Office Action issued in Indian Patent Application No. 3334/DELNP/2009.
May 24, 2017 Office Action issued in European Patent Application No. 13771208.9.
May 15, 2017 Office Action issued in Japanese Patent Application No. 2015-533703.
Jun. 15, 2017 Office Action issued in U.S. Appl. No. 14/445,626.
Mar. 14, 2017 Office Action issued in U.S. Appl. No. 14/581,549.
Oct. 26, 2016 Office Action issued in Application No. 201210084254.7.
Aug. 28, 2017 Office Action Issued in U.S. Appl. No. 14/581,549.
Nov. 17, 2017 Office Action issued in U.S. Appl. No. 14/445,626.
Apr. 2, 2018 Examiner's Answer issued in U.S. Appl. No. 14/581,549.
Jun. 8, 2018 Office Action issued in US. Appl. No. 14/445,626.

(56) References Cited

OTHER PUBLICATIONS

Jan. 10, 2018 Office Action issued in Chinese Patent Application No. 201510612697.2.
Jan. 30, 2019 Office Action issued in U.S. Appl. No. 14/445,626.
"Linear Incision Technique—Procedure and clinical results," BAHA Clinical Review.

* cited by examiner

IMPLANTABLE FLUID ROUTER

The present invention relates to implantable drug delivery apparatus for neurosurgical applications and in particular to an implantable fluid router that comprises a gas vent.

Implantable drug delivery systems are known for the treatment of neurological conditions where the blood brain barrier prevents many systemically administered drugs from reaching the desired target, or where the delivery of drugs or therapeutic agents to targets other than the desired target may produce unacceptable side affects. In particular, it is known to deliver drugs and other therapeutic agents directly into the brain parenchyma via one or more implanted catheters. Examples of this type of therapy include the infusion of gamma-amino-butyric acid agonists into an epileptic focus or pathway that will block its transmission, the delivery of cytotoxic agents directly into a brain tumour, and the infusion of neurotrophic agents for the protection and repair of failing or damaged nerve cells. The infusion of such neurotrophic agents can be used to treat a variety of neurodegenerative disorders including Parkinson's disease, Alzheimer's disease and Amyotrophic Lateral Sclerosis, and may also be useful in stimulating the repair of damaged neural tissue after injury from trauma, stroke or inflammation.

Fully implantable neurological drug delivery systems have been used for many years. A pump is typically located in the abdomen and tubing is tunnelled subcutaneously to implanted intraparenchymal catheters. It is known for the pumps used in such systems to include bacterial filters, for example see GB2389791 or WO2009/128959

According to a first aspect of the present invention, an implantable fluid router is provided that comprises one or more inlets, one or more outlets and at least one gas vent for removing gas from liquid routed from the one or more inlets to the one or more outlets. The at least one gas vent of the fluid router acts to remove bubbles of gas (typically air) from any liquid that is being routed from an inlet to an outlet. The removal of air from liquid in such a manner prevents air bubbles occluding catheters located downstream of the fluid router thereby improving treatment efficacy and reliability.

Advantageously, the implantable fluid router comprises a plurality of inlets, a plurality of outlets and a plurality of separate liquid pathways between the plurality of inlets and the plurality of outlets. Preferably, the router comprises a plurality of gas vents. Advantageously, each liquid pathway comprises a separate gas vent. In this manner separate fluid pathways through the router, with separate gas vents, are provided. Such a device may be used to separately connect the different lumen of a multi-lumen supply tube (or multiple single lumen supply tubes) to multiple catheters.

The implantable fluid router may comprise one inlet, one outlet and one gas vent in the liquid pathway between the inlet and the outlet. Advantageously, such a router may be provided in the form of catheter head. In other words, an implantable catheter device may be provided that comprises the fluid router. For example, the fluid router may be integrally formed in the head of the catheter. Preferably, such a catheter device comprises a neurosurgical catheter device (e.g. for direct insertion into the brain parenchyma). The present invention thus extends to a neurosurgical catheter comprising an implantable router unit.

Gas exiting each gas vent may be routed to the outside of the body. For example, a tube may be connected to each gas vent that is in fluid communication with the outside of the body. A return vent line may thus be provided. For example, a flow tube may supply fluid to the implantable fluid router and a return tube may carry any air that is removed from that fluid by the gas vent. Preferably, each gas vent of the fluid router is arranged to vent gas into the body of the subject in which the device is implanted. In other words, the fluid router may comprise an aperture or membrane through which gas extracted from the liquid may exit. Any such gas may then enter the body where it is naturally absorbed.

Each gas vent of the fluid router preferably includes a chamber. Each chamber advantageously comprises a gas permeable membrane through which gas present in liquid routed through the filter chamber may pass. Preferably, the gas permeable membrane is hydrophobic. The gas permeable membrane may comprise expanded polytetraflurothylene (ePTFE). Each chamber may also comprise a hydrophilic material through which liquid passes when routed through that filter chamber. The hydrophilic material is preferably bacteria retentive and thereby also acts as a bacterial filter. In this manner, the fluid router acts as both a gas and bacterial filter. It is preferred that the liquid routed from the one or more inlets to the one or more outlets comprises a therapeutic agent. This may be supplied from an implanted pump or from an external (to the body) pump. In a preferred embodiment, the fluid is supplied to the fluid router via a percutaneous access device.

A neurosurgical kit may be provided that comprises the above described implantable router. The kit may also include at least one of a neurosurgical catheter, a supply tube and a percutaneous access device.

There is thus described herein an implantable router unit that comprises one or more inlets and one or more outlets, wherein fluid is routable from the one or more inlets to the one or more outlets, wherein the router unit comprises an air filter for removing air from fluid routed from the one or more inlets to the one or more outlets. The implantable router unit may also include a bacterial filter. Preferably, the implantable router unit comprises a plurality of inlets that are each separately connected to one of the plurality of outlets. If the implantable router unit has a plurality of separate fluid paths therethrough (e.g. if it comprises a plurality of inlets that are each connected to one of a plurality of outlets) it is preferred that separate air filtration is applied to each fluid path. For example, each fluid path may include a separate filter chamber. Conveniently, the filter (e.g. each filter chamber) comprises a hydrophobic layer and a hydrophilic layer to provide a gas (e.g. air) venting or filtering function. In other words, the filter separates and removes any gas (e.g. air) from the liquid therapeutic agent being delivered. A membrane or diaphragm may also be provided (e.g. adjacent the hydrophobic layer) through which any vented air dissipates into the body cavity. The implantable router unit may be provided as part of a catheter device. For example, an implantable router unit having a single inlet and single outlet may be incorporated in the head of an intra-parenchymal catheter.

Figure 2:
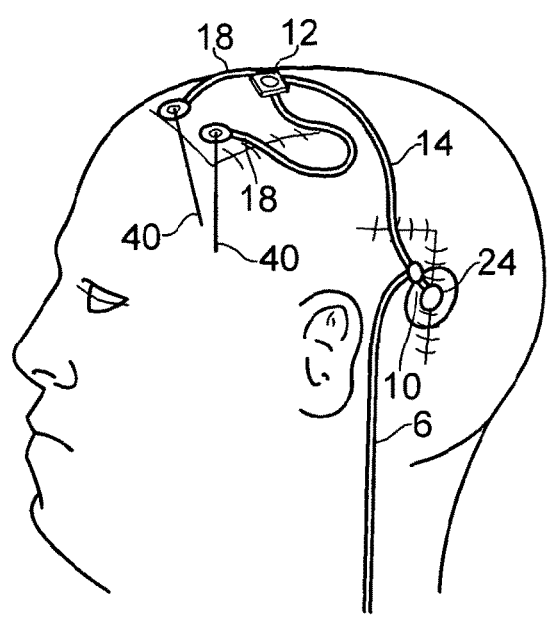
Figure 3:
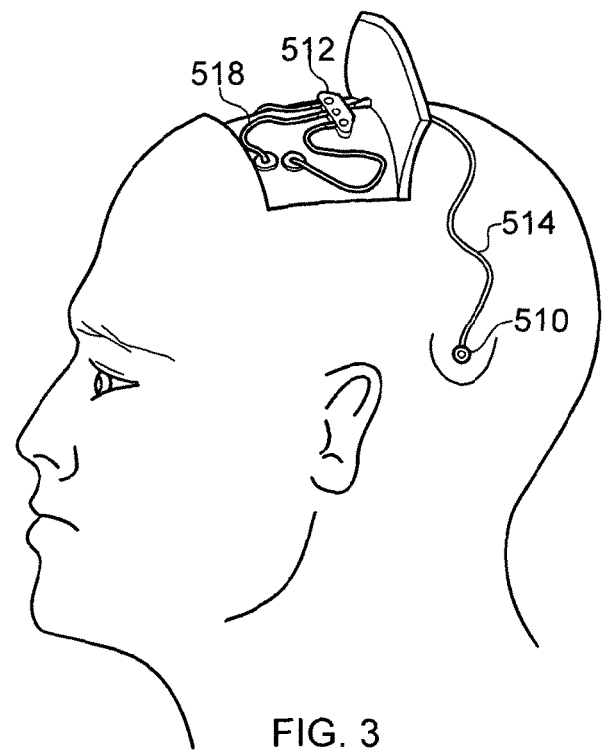
Figure 4:
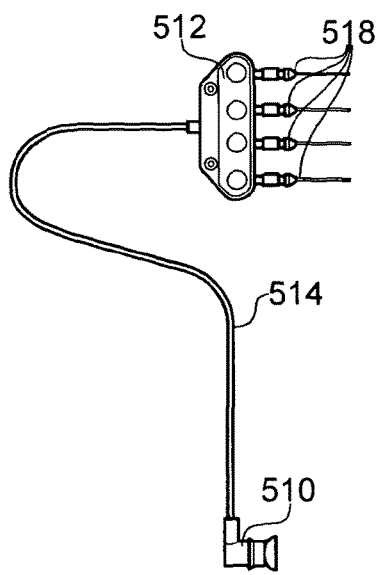
Figure 5:
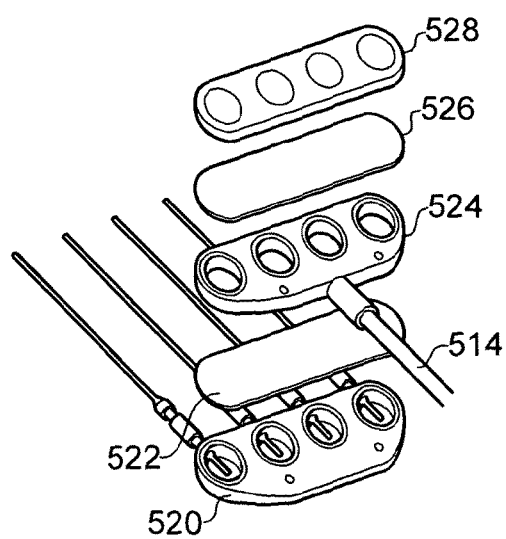
Figure 7:
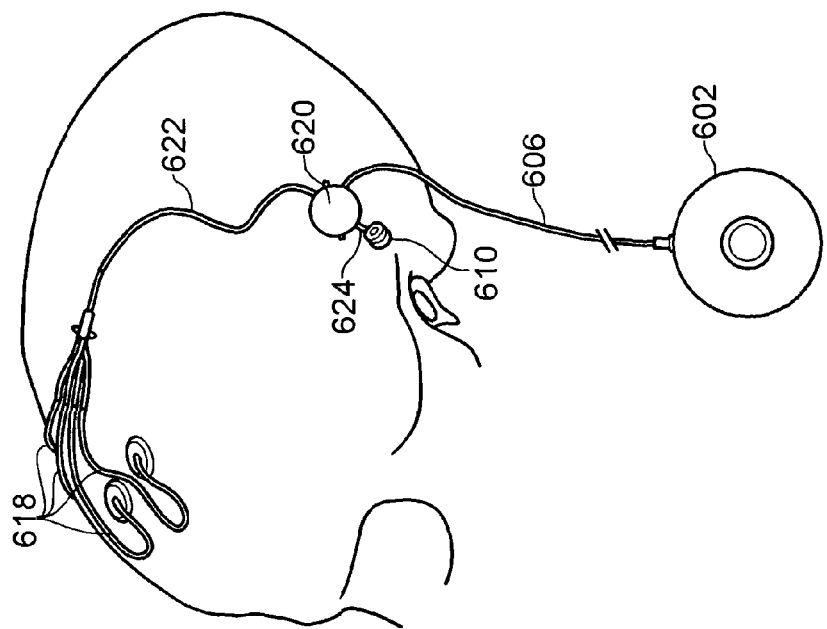
Figure 6:
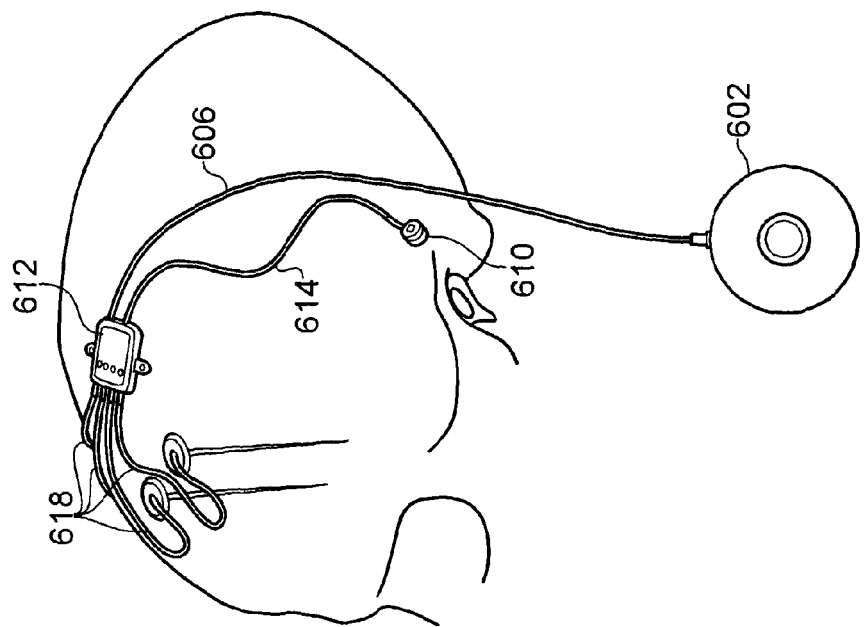
Figure 8:
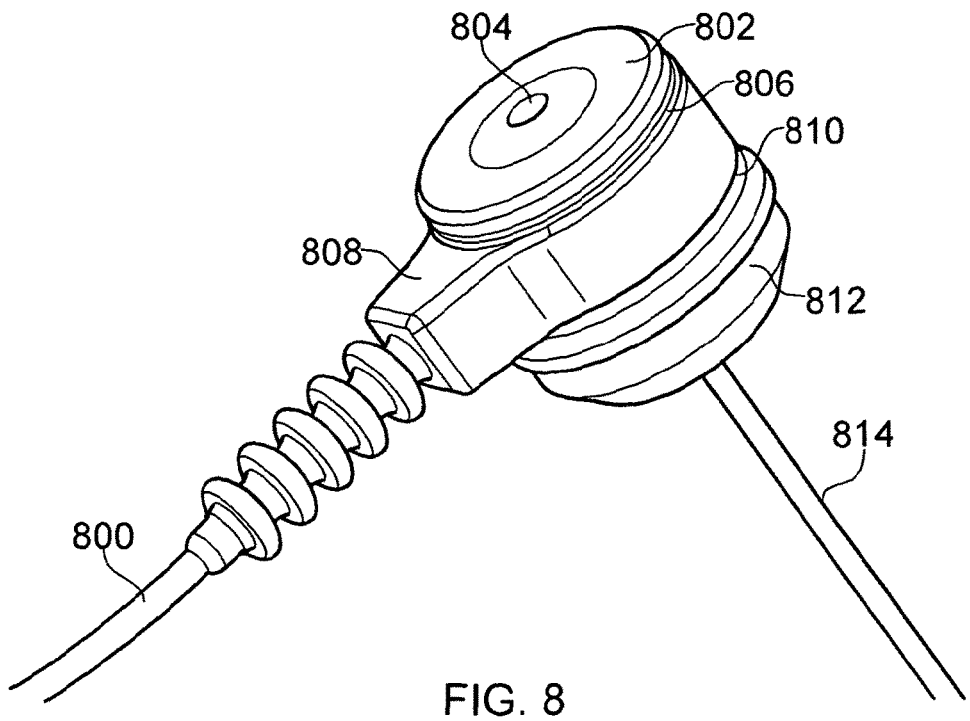
Figure 9:
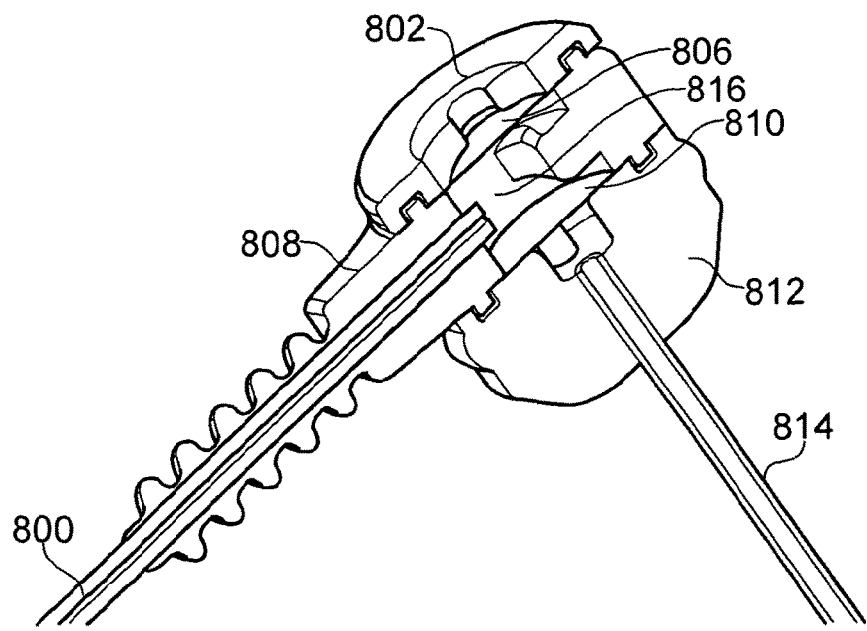
Figure 10:
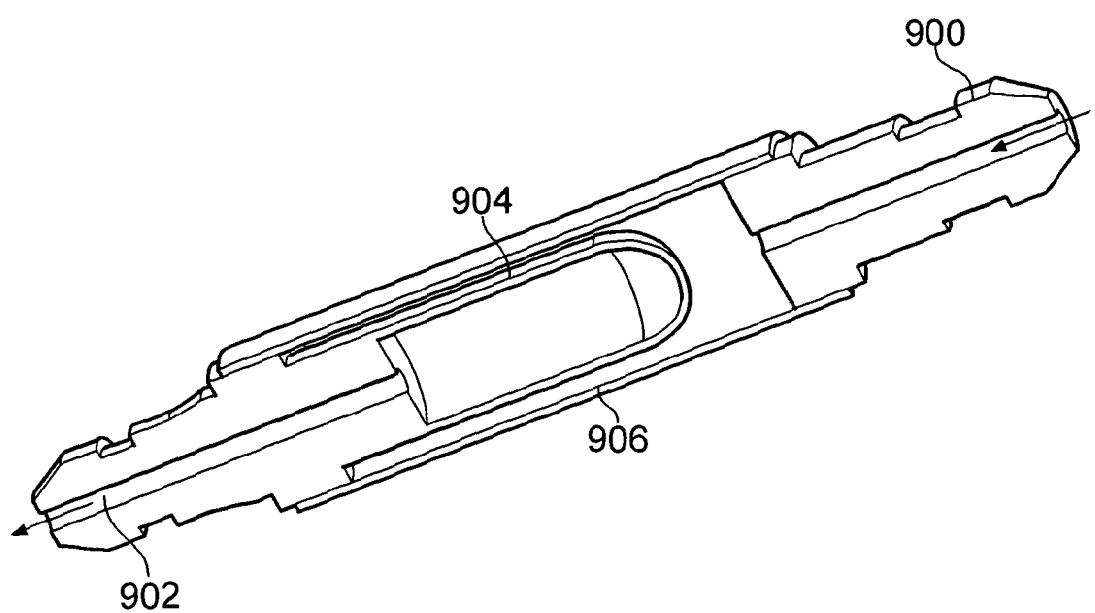

The invention will now be described, by way of example only, with reference to the accompanying drawings in which;

FIG. 1 shows implantable neurological drug delivery apparatus that includes a fluid router of the present invention, FIG. 2 illustrates the device of FIG. 1 implanted in a subject, FIG. 3 shows a further implantable neurological drug delivery apparatus, FIG. 4 shows the air/bacterial filter and percutaneous drug delivery port of the apparatus of FIG. 3, FIG. 5 is an exploded view of the air/bacterial filter shown in FIGS. 3 and 4, FIG. 6 shows a further implantable neurological drug delivery apparatus, FIG. 7 illustrates a further implantable neurological drug delivery apparatus having a separate filter unit, FIG. 8 shows a catheter device having an integral air vent, FIG. 9 shows a cut away view of the catheter device of FIG. 8, and FIG. 10 shows an in-line fluid router having an air vent.

Referring to FIG. 1, implantable neurological drug delivery apparatus is shown. The apparatus comprises a constant pressure pump 2 that includes an internal reservoir and has an outlet 4 connected to the first end of a single lumen supply tube 6. Although a constant pressure pump 2 is shown, it should be noted that any implantable pump (e.g. a constant or programmable flow rate pump) can be employed. The second end of the supply tube 6 is connectable to the inlet 8 of a port unit 10. The port unit 10 comprises two outlets that are linked to the two inlets of a router unit 12 by a dual-lumen supply tube 14. The router unit 12 comprises two outlets 16, each in fluid communication with a respective lumen of the supply tube 14, that are each connectable to a neurological catheter device 18.

The port unit 10 comprises a subcutaneous portion 20 and a percutaneous portion 22 that has an extracorporeal surface 24. The subcutaneous portion 20 is suitable for at least partial insertion into an appropriately shaped recess formed in the skull. In particular, the subcutaneous portion 20 is coated with a material that promotes biointegration with bone after implantation and will thus become secured to the skull without the need for bone screws or the like. In other words, the subcutaneous portion 20 is osseointegrating (also termed osteointegrating). In this example, the coating provided on the external surface of the subcutaneous portion 20 comprises plasma sprayed titanium combined with hydroxyapatite. Other coatings or surface finishes may be provided to produce a similar effect.

The subcutaneous portion 20 may be formed as a single component but comprises three discrete functional parts. In particular, a first substantially cylindrical part 26 of the subcutaneous portion 20 is connected to a second substantially cylindrical part 28 by an elongate joining section 30. As will be described in more detail below with reference to FIG. 3, the second substantially cylindrical part 28 has an inlet 8 for receiving carrier fluid from the pump outlet 4 and an exit for a dual-lumen supply tube 14 that comprise a separate lumen for supplying fluid to each of the two catheters 18 via the router unit 12. The first substantially cylindrical part 26 is also attachable to the percutaneous portion 22 thereby allowing external access to the separate fluidic pathways to the two catheter devices 18. In particular, the extracorporeal surface 24 comprises two sealed access ports that permit fluid (e.g. a drug or other therapeutic agent) to be injected into the fluid stream that runs from the pump 2 to the catheter devices 18.

An external fluid connector unit 23 is also provided that is releasably attachable to the extracorporeal surface 24 of the percutaneous portion 22. When the connector unit 23 is attached or mated with the port unit 10, a pair of protruding needles 29 penetrate the seal and thereby provide separate fluidic access to the two ports of the port unit 10. The needles of the fluid connector unit 23 may be separately connected to different channels of an external drug pump 27 or individual pumps via a multi-lumen tube 25. In this manner, the fluid connector unit 23 provides separate fluidic access to the different ports of the port unit 10 to enable the delivery of therapeutic agents or the like to the catheter devices 18. The fluid connector unit 23 may be attachable to the extracorporeal surface 24 in only one orientation to ensure the same needle always accesses the same port. A locking mechanism may also be provided to lock the fluid connector unit 23 to the extracorporeal surface 24 as and when required.

The first substantially cylindrical part 26 is connected to the second substantially cylindrical part 28 by the elongate joining section 30. The elongate joining section 30 comprises multiple lumens (in this case three) that provide the necessary fluidic pathways between the first and second substantially cylindrical parts 26 and 28. In addition, the provision of such an elongate joining section 30 has the benefit of reducing the infection risk. Infection risk is further reduced by spacing the port unit 10 apart from the router unit 12. The port unit and the various advantages thereof are described in more detail in Applicant's co-pending PCT application filed on the same day as the present application and also claiming priority from British patent application No. 1002370.3.

Referring to FIG. 2, the drug delivery apparatus described with reference to FIG. 1 is illustrated when implanted in the body. The constant pressure pump 2, which may comprise a diaphragm pump of known type, is not shown in FIG. 2 but is implanted in the abdomen. The supply tube 6 running from the pump 2 is tunnelled under the skin to the head of the subject. The port unit 10 is affixed within an appropriately dimensioned recess formed in the bone of the skull adjacent the ear. The supply tube 6 is connected to the inlet 8 of the port unit 10 and the dual-lumen supply tube 14 exiting the port unit 10 is subcutaneously tunnelled under the scalp to the router unit 12. The router unit 12 is secured to the skull, for example using bone screws, in the vicinity of the point where the catheter devices 18 pass through holes in the skull and enter the brain parenchyma.

The constant pressure pump 2 contains a reservoir that stores a carrier fluid, such as saline (e.g. buffered saline) or artificial cerebrospinal fluid (CSF). The pump 2 may be refillable in a known manner by percutaneous injection into a refill port provided on a surface of the pump 2. After implantation, the pump 2 supplies carrier fluid under pressure to the port unit 10 via the supply tube 6. The port unit 10 is arranged to continuously direct a small flow of carrier fluid to each of the catheter devices 18 via the dual-lumen supply tube 14 and router unit 12. The distal end 40 of each catheter device 18 is accurately positioned within the brain parenchyma at a required target site. Examples of suitable catheter devices are described in WO03/077785. Techniques for locating the catheters adjacent the required target sites in the brain are described in U.S. Pat. No. 6,609,020 and WO03/077784. The contents of these documents are hereby incorporated by reference.

For the majority of the time after implantation, the drug delivery apparatus is arranged to pump small volumes of carrier fluid into the brain parenchyma via the catheter devices 18. The constant, or substantially constant, flow of carrier fluid reduces the chance of the catheter devices 18 becoming occluded due to tissue in-growth. This allows the chronic implantation of catheter devices that include fine tubes having an outer diameter of less than 0.25 mm. When the delivery of therapeutic agents is required, the extracorporeal surface 24 of the percutaneous portion 22 of the port unit 10 provides separate access to the fluidic pathways to each catheter device 18 and thus permits the required dosage of therapeutic agent to be delivered to the target site(s). Such delivery of therapeutic agent may be performed continuously (e.g. over a period of a few hours or days) through each catheter in parallel. Alternatively, the delivery of therapeutic agent may be performed serially (e.g. through each catheter in turn) to minimise any side effects associated with the delivered agent.

For many years, fully implantable drug delivery systems have been preferred for neurological applications to minimise the chances of an infection bypassing the blood-brain barrier and entering the brain parenchyma at the point the barrier is penetrated by a catheter. Such fully implantable system have however been found to have a number of disadvantages; for example, the storage capacity can be limited and problems often arise delivering drugs that have a short shelf-life or need to be stored in a certain environment (e.g. at a certain temperature). The use of a single implanted pump also does not provide the flow control that is needed when delivering fluid in precise volumes to different site using multiple catheters. It can also be difficult to access a refill port of a subcutaneously implanted pump, especially in obese patients, and any subcutaneous leakage of therapeutic agent can provoke an immune response to such agents. Although percutaneous access ports or refill ports have been proposed previously, such ports tend to be implantable in the torso, thereby requiring long lengths of supply tubing that increase the dead volume of the system. This additional dead volume can reduce the control over drug delivery thereby reducing treatment efficacy in certain circumstances.

The drug delivery apparatus illustrated in FIGS. 1 and 2 includes a port unit 10 that attached to the skull, but the apparatus is configured such that the inclusion of the percutaneous portion 22 does not introduce an unacceptable increase in the risk of an infection bypassing the blood-brain barrier. A number of features of the apparatus minimise this infection risk and some or all of such features may be included in the apparatus as required.

The subcutaneous portion 20 of the port unit 10 comprises a first substantially cylindrical part 26 that is connected to the second substantially cylindrical part 28 by the elongate joining section 30. As explained below, the majority of the subcutaneous portion 20 is located in a recess formed in the skull bone. In particular, the majority of the elongate joining section 30 is buried within the slot or recess formed in the skull. Preferably, the elongate joining section 30 is sub-flush to the outer surface of the skull bone and bone chipping or the like are placed on top of the elongate joining section 30 after implantation. This allows bone to regrow over the top of the elongate joining section 30 after implantation. After such bone growth, the first substantially cylindrical part 26 is separated from the second substantially cylindrical part 28 by a region that is buried within the skull bone. This acts as a infection barrier between the supply tube connections and the percutaneous part of the port unit 10 where infection is most likely to occur. In other words, the arrangement reduces the chance of any infection that arises at the interface between the skin and the protruding percutaneous portion 22 from passing to the supply tube 14 and migrating along the outer surfaces of the various tubes that lead to the catheter devices that bypass the blood-brain barrier. Furthermore, the size of the percutaneous part of the port unit 10 is minimised thereby reducing the size of incision required thereby further reducing the infection risk.

In addition, it can be seen that the router unit 12 is located away from the port unit 10. In this example, the router unit 12 is separated from the port unit 10 by about 15 cm of dual-lumen tubing 14. As noted above the most likely infection site is the interface between the skin and the percutaneous portion 22 of the port unit 10. Providing the router unit 12 between the tubing from the port unit 10 and the catheter devices 18 thus introduces a further barrier to infection.

Bacterial filters may be provided within the apparatus to remove any bacteria present in the carrier fluid or in the therapeutic agent that is delivered. A bacterial filter may, for example, be located in the port unit 10 (e.g. in the second substantially cylindrical part 28) and/or in the router unit 12. The pump 2 may also or alternatively include a bacterial filter. The apparatus may also comprise an air filter to remove any air bubbles present in the fluid delivered to the brain. Such air bubbles are most likely to arise at connections between tubes or at the point of infusion of therapeutic agent into the port unit 10. In this example, the air filter is located in the router unit 12 so that it is close to the catheter devices 18 thereby removing as much air from the apparatus as possible. Alternatively, or additionally, such air filters may be provided in the port unit 10, for example in the second substantially cylindrical part 28, or as part of the catheter device. Air extracted from the fluid by the air filters may be released into the body where it is absorbed. Alternatively, an air return path may be provided to outside of the body via the port unit 10 and connector 23.

FIGS. 3 to 5 show further neurological apparatus that comprises a port unit 510, a supply tube 514, a router unit 512 and four catheter devices 518. In particular, FIG. 3 shows the apparatus implanted in a subject, FIG. 4 illustrates the apparatus prior to implantation and FIG. 5 show the components of the filter unit in more detail.

Referring to FIGS. 3 and 4, it can be seen how the port unit 510 is connected to the router unit 512 by the supply tube 514. The catheter devices 518 are each linked to an outlet of the router unit 512 that provides an air filtering function.

Referring to FIG. 5, the structure of the router unit 512 is shown in more detail. The router unit 512 comprises a four chamber outflow portion 520, a hydrophilic (bacterial) filter 522, a four chamber inflow portion 524, a hydrophobic (gas permeable) filter 526 and a diaphragm membrane 528. As described in more detail below, fluid passed to the router unit 512 through the four lumens of the supply tube 514 is separately filtered and output via outlets 530 to the respective catheter devices 518. In other words, each fluid path through the router unit is separately filtered and there is no mixing of the fluid that is routed to the different catheter devices 518.

In operation, fluid from each lumen of the supply tube 514 passes to a respective one of the inflow chambers of the inflow portion 524. The liquid of the fluid is attracted to the hydrophilic filter 522 and passes through that hydrophilic filter 522 into the associated outflow chamber of the outflow portion 520. Gas (e.g. air) does not pass through the hydrophilic filter 522. Fluid from each chamber of the outflow portion 520 passes to an outlet 530 that is in turn connected to a catheter device 518. The hydrophobic filter 526 acts as a barrier to liquid, but allows any gas (e.g. air) bubbles to pass through it. Gas (e.g. air) is thus removed from the fluid and is allowed to dissipate through the diaphragm membrane 528 into the body. The hydrophilic filter 522 may also be configured to provide a bacterial filtration function.

As can be seen from FIG. 13, the router unit 512 is located as close to the catheter devices 518 as possible. This ensures air removal is performed as far downstream as possible thereby minimising the amount of air that is present in the fluid expelled from the catheter devices 518. In particular, the air filtration is performed away from the port unit 510 and the majority of the tube connections that could introduce air.

Referring to FIG. 6, a further embodiment of neurological apparatus of the present invention is shown. The apparatus comprises an abdominally implantable constant pressure pump 602, a percutaneous port unit 610, a router unit 612 and catheter device 618. A single lumen supply tube 606 supplies carrier fluid from the pump 602 to the router unit 612. A four lumen supply tube 614 provide four separate fluid pathways from the port unit 610 to the router unit 612. The port unit 610 is preferably a port unit of the type described with reference to FIG. 4. The apparatus is arranged so that a flow of fluid supplied by the abdominal pump 602 is continuously pumped, at a low flow rate, to the catheter devices 618 to prevent occlusion of such devices. Fluid containing a therapeutic agent may also be pumped into the port unit 610 and directed to each catheter device 618 via the router unit 612. The router unit 612 includes a bacterial filter and/or an air filter.

FIG. 7 illustrates a variant of the device described with reference to FIG. 6. Carrier fluid from an abdominal pump 602 is pumped to a filter unit 620 via a single lumen supply tube 606. The filter unit 620 splits the received carrier fluid into four streams that are routed into the four lumens at the proximal end of the supply tube 622. At the distal end of the supply tube 622, the four lumens separate into four separate tubes that are each connected to a catheter device 618. The port unit 610 is connected to the filter unit 620 by a four lumen supply tube 624 and provides four separate fluidic links to the four separate fluid streams through the filter unit 620. Therapeutic agent may thus be pumped to any one of the catheter devices 618 from the port unit 610.

Referring next to FIGS. 8 to 9, a catheter device is illustrated in which a fluid router comprising an air vent is located in the catheter head. This enables gas (e.g. air) to be separated from the liquid being delivered at a point that is even closer to the point of delivery.

FIG. 8 shows a catheter device that comprises a supply tube 800, a filter top plate 802 having an aperture 804 formed therein, a hydrophobic filter membrane (gas vent) 806, a filter body middle section 808, a bacteria retentive hydrophilic filter membrane 810, a filter base section 812 and an fine tube 814 for insertion into the brain parenchyma. The various components of the catheter are also shown in the cut-away view of FIG. 9, where the internal chamber 816 can also be seen.

Fluid (typically a liquid that contains unwanted air bubbles and bacteria) is supplied under pressure to the catheter device via the supply tube 800 and enters the chamber 816. Liquid exits the chamber via the hydrophilic filter membrane 810 (noting any bacteria in the fluid are retained by the filter membrane 810) and passes into the fine tube 814. This liquid is then expelled from the distal end of the fine tube 814 to the desired site in the body. Any air bubbles contained in the fluid collect at, and diffuse through, the hydrophobic filter membrane 806. The air then exits the device via the aperture 804 in the filter top plate 802. The relatively small amount of air that is vented from the fluid is then simply absorbed naturally by the body.

The catheter device alone may be inserted into the brain parenchyma or the catheter may be inserted via a previously implanted guide tube. Once implanted, the catheter device may be subcutaneously buried and either used periodically or continuously to deliver therapeutic agents directly to the brain parenchyma. Guide tubes and associated methods for inserting neurosurgical catheters are described in U.S. Pat. No. 6,609,020 and WO2003/077785. A skull mount for use when inserting catheter devices is also described in WO2009/047494. The methods described previously may also be used to implant the catheter device described herein with reference to FIGS. 8 and 9.

It is convenient for the gas vent to be included in a fluid router unit having multiple inlets/outlets or the head of catheter device as described above. It would, however, be appreciated by the skilled person that the gas vent could be included in any part of an implantable apparatus or as a standalone implantable component.

Referring to FIG. 10, an implantable in-line bubble filter device is illustrated. The device comprises an inlet 900, an outlet 902, a hydrophilic (bacteria retaining) membrane 904 and an outer gas permeable (hydrophobic) membrane 906 fabricated from expanded polytetrafluroethylene (ePTFE). ePTFE has the additional advantage that it can be processed so that cells do not grow or adhere to it. Although not shown, an outer protective mesh may be provided. The device may be included as part of an implantable drug delivery system.

The skilled person would appreciate that, in addition to the examples outlined above, the gas vents of the present invention may be implemented using a variety of different materials. For example, polyvinylidene fluoride (PVDF) or polyethersulfone (PES) membranes may be provided that can be either hydrophobic or hydrophilic. Sintered titanium, for example plugs, cups or tubes of porous titanium, may also be used for bacteria retention. The various materials outlined above should therefore be in no way seen as limiting the scope of the present invention. Similarly, the gas vent may be incorporated into any medical, implantable, device and the various embodiments presented above are in no way intended to limit the scope of the invention.

The invention claimed is:

1. An implantable fluid router comprising:
   at least one inlet;
   at least one outlet; and
   at least one filter chamber connecting the inlet to the outlet, the filter chamber comprising a hydrophilic filter membrane and a gas permeable membrane and being configured to separate liquid and gas from a fluid by (i) passing liquid in the fluid received from the inlet through the hydrophilic filter membrane to the outlet, and (ii) passing gas in the fluid received from the inlet through the gas permeable membrane in order to vent the gas from the filter chamber.

2. An implantable fluid router according to claim 1, comprising a plurality of inlets, a plurality of outlets and a plurality of separate fluid pathways between the plurality of inlets and the plurality of outlets.

3. An implantable fluid router according to claim 2, comprising a plurality of filter chambers, wherein each fluid pathway comprises a separate filter chamber.

4. An implantable fluid router according to claim 1, comprising one inlet, one outlet and one filter chamber in a fluid pathway between the one inlet and the one outlet.

5. An implantable fluid router according to claim 4, provided in the form of catheter head.

6. An implantable fluid router according to claim 1, wherein each filter chamber is configured to vent gas into a body of a subject in which the fluid router is implanted.

7. An implantable fluid router according to claim 1, wherein the gas permeable membrane is hydrophobic.

8. An implantable fluid router according to claim 1, wherein the gas permeable membrane comprises expanded polytetrafluorothylene (ePTFE).

9. An implantable fluid router according to claim 1, wherein the hydrophilic filter membrane includes a hydrophilic material configured to retain and filter bacteria.

10. An implantable fluid router according to claim 1, wherein the fluid comprises a therapeutic agent.

11. A neurosurgical catheter comprising an implantable router unit according to claim 1.

12. A neurosurgical kit comprising an implantable router according to claim 1 and at least one of a neurosurgical catheter, a supply tube and a percutaneous access device.

13. An implantable fluid router according to claim 1, wherein a return tube is connected to each filter chamber to carry gas that is removed from the fluid.

14. An implantable fluid router according to claim 13, wherein, when implanted, the return tube is in fluid communication with the outside of a body of a subject thereby allowing gas exiting the filter chamber to be routed to outside of the body.

15. An implantable fluid router according to claim 13, comprising a plurality of inlets, a plurality of outlets and a plurality of separate fluid pathways between the plurality of inlets and the plurality of outlets.

16. An implantable fluid router according to claim 15, comprising a plurality of filter chambers, wherein each fluid pathway comprises a separate filter chamber.

17. An implantable fluid router according to claim 1, wherein the filter chamber is configured to separate the liquid and gas from the fluid in-line as it flows from the inlet to the outlet.

\* \* \* \* \*